United States Patent
Scalzo

[11] Patent Number: 5,807,101
[45] Date of Patent: Sep. 15, 1998

[54] UNIVERSAL OCCLUSAL MATRIX

[76] Inventor: Josephine Scalzo, 4205-46 Ave., Red Deer, Alberta, Canada, T4N 3M7

[21] Appl. No.: 586,372

[22] Filed: Jan. 17, 1996

[51] Int. Cl.$^6$ ..................................................... A61C 5/00
[52] U.S. Cl. ................................ 433/39; 433/40; 433/226
[58] Field of Search .......................... 433/37, 39, 217.1, 433/218, 219, 221, 222.1, 226, 227, 40, 228.1

[56] References Cited

U.S. PATENT DOCUMENTS

| | | | |
|---|---|---|---|
| 853,984 | 5/1907 | Lauderdale | 433/40 |
| 2,237,926 | 4/1941 | Cooley | 433/40 |
| 3,421,222 | 1/1969 | Newman | 433/39 |
| 3,422,535 | 1/1969 | Johnson | 433/218 |
| 3,949,477 | 4/1976 | Cohen et al. . | |
| 3,974,567 | 8/1976 | Ridgeway | 433/217.1 |
| 4,303,389 | 12/1981 | Salsarulo | 433/40 |
| 4,445,858 | 5/1984 | Johnson | 433/141 |
| 4,449,928 | 5/1984 | von Weissenfluh | 433/40 |
| 4,571,188 | 2/1986 | Hamilton | 433/226 |
| 4,600,389 | 7/1986 | Schwartz | 433/217.1 |
| 4,718,849 | 1/1988 | von Weissenfluh et al. | 433/229 |
| 4,909,736 | 3/1990 | Ritter | 433/39 |
| 4,957,441 | 9/1990 | Bryan | 433/226 |
| 5,007,837 | 4/1991 | Werly | 433/226 |
| 5,183,397 | 2/1993 | Weissman | 433/218 |
| 5,332,390 | 7/1994 | Rosellini | 433/222.1 |
| 5,547,379 | 8/1996 | Hasel | 433/217.1 |

FOREIGN PATENT DOCUMENTS

| | | | |
|---|---|---|---|
| 85027 | 8/1983 | European Pat. Off. | 433/228.1 |
| 626247 | 11/1981 | Switzerland | 433/228.1 |

*Primary Examiner*—Ralph Lewis
*Attorney, Agent, or Firm*—Anthony R. Lambert

[57] ABSTRACT

A universal occlusal matrix for application to the occlusal surface of a tooth having a central groove forming a V-shape in cross-section, the universal occlusal matrix being transparent to ultraviolet rays and to rays of the visible spectrum to permit rapid hardening by polymerization of the filling material and of a material which does not adhere to that of the said filing. The universal occlusal matrix has an elastic lamina having a central groove forming a V-shape in cross-section with first and second curved concave wings extending outward from the central groove. The elastic lamina extends away from the central groove sufficiently far to cover the occlusal surface of the various teeth to which it may be applied. The angle of the V-shape of the groove of the lamina is greater than the angle of the V-shape of the groove of the various teeth to which it may be applied. The elastic lamina is characterized by having wings whose radius of curvature is less than the radius of curvature of the cusps of the various teeth to which it may be applied.

11 Claims, 1 Drawing Sheet

UNIVERSAL OCCLUSAL MATRIX

FIELD OF THE INVENTION

The invention relates to transparent matrices used in the filling of teeth.

BACKGROUND OF THE INVENTION

Cervical matrices for dental use are already known, transparent to ultraviolet rays and to the rays of the visible spectrum, of material which does not adhere to that of the filling, each characterized by a transparent plate preferably made of plastic material, bent to adhere perfectly to the shape of the tooth in course of filling, or being made from a concave elastic lamina with a radius of curvature less than that of the different teeth to which it can be applied and thinned at the end to be able to penetrate under the gum, the lamina being provided at the rear with a stem in order to be able to grasp it with forceps and press it strongly against the tooth to be treated so that by increasing its radius of curvature it can be adapted perfectly to the shape of the tooth to which it is applied. See U.S. Pat. No. 4,449,928.

In addition, it is known to provide a custom occlusal matrix in which a matrix is created by applying a polymer to the occlusal surface of a tooth, allowing it to set, removing it, applying dental material to a cavity and then placing the matrix over the dental material to help hold the material in the cavity with the desired occlusal surface pattern.

The inventor has determined that the principles of making the aforementioned universal cervical matrix cannot be readily adapted to an occlusal matrix. If the radius of curvature of an occlusal matrix is too great on either side of a groove in the center of the matrix, with a sharp V bend at the groove, the material of the matrix at the center of the matrix tends to push down into the central groove of the tooth and force filling out of the cavity being treated. Therefore, the inventor has provided a novel universal occlusal matrix that helps avoid the forced removal of filling material from the cavity being treated.

Therefore, in accordance with one aspect of the invention, there is provided a universal occlusal matrix for application to the occlusal surface of a tooth having a central groove forming a V-shape in cross-section, the universal occlusal matrix being transparent to ultraviolet rays and to rays of the visible spectrum to permit rapid hardening by polymerization of the filling material and of a material which does not adhere to that of the said filing, the universal occlusal matrix being characterized by:

an elastic lamina having a central groove forming a V-shape in cross-section with first and second curved concave wings extending outward from the central groove;

the elastic lamina extending away from the central groove sufficiently far to cover the occlusal surface of the various teeth to which it may be applied; and the angle of the V-shape of the groove of the lamina being greater than the angle of the V-shape of the groove of the various teeth to which it may be applied.

In addition, in another aspect of the invention, the elastic lamina is characterized by having wings whose radius of curvature is less than the radius of curvature of the cusps of the various teeth to which it may be applied.

Similar principles of construction are applied for other grooves, fossa, pits, cusps and ridges on the teeth to which the elastic lamina may be applied.

These and other aspects of the invention may be found in the detailed description and claims that follow.

BRIEF DESCRIPTION OF THE DRAWINGS

There will now be described preferred embodiments of the invention, with reference to the drawings, by way of illustration, in which like numerals denote like elements and in which.

DETAILED DESCRIPTION OF PREFERRED EMBODIMENTS

Figure 1:
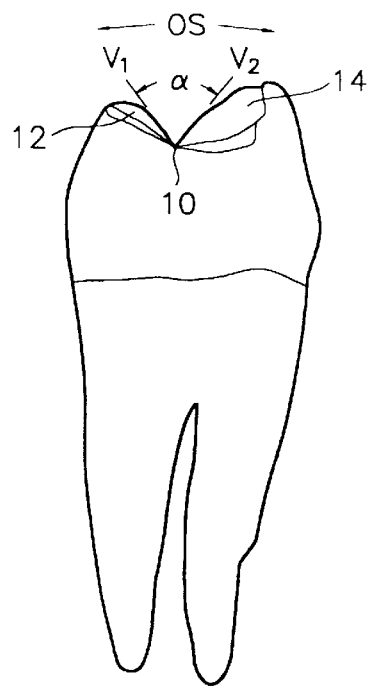
FIG. 1 is a distal view of a maxillary first premolar.

Referring to FIG. 1, the maxillary first premolar shown here is exemplary of the various teeth to which the universal occlusal matrix of the invention may be applied. The occlusal surface is illustrated by the area under the line OS, and has a central occlusal groove 10 having a V-shape defined by lines $V_1$ and $V_2$. The angle of the V-shape is given by the angle $\alpha$ between the lines $V_1$ and $V_2$. The central groove 10, as is well known to any dentist, and as described at pages 48–74 of "Dental Anatomy and Occlusion", Williams and Wilkins, Baltimore, 1969, the content of all of which is hereby incorporated herein by reference, terminates mesially in the mesial triangular fossa and pit, from which diverges the mesio-buccal groove and mesiolingual groove. Between the mesiolingual groove and the mesio-buccal groove lies the mesial marginal ridge. Similarly, the central occlusal groove 10 terminates distally in the distal triangular fossa and pit, from which diverges the disto-buccal groove and distolingual groove. Between the distolingual groove and the disto-buccal groove lies the distal marginal ridge. On either side of the central occlusal groove lies the buccal cusp 14 and lingual cusp 12.

Figure 2:
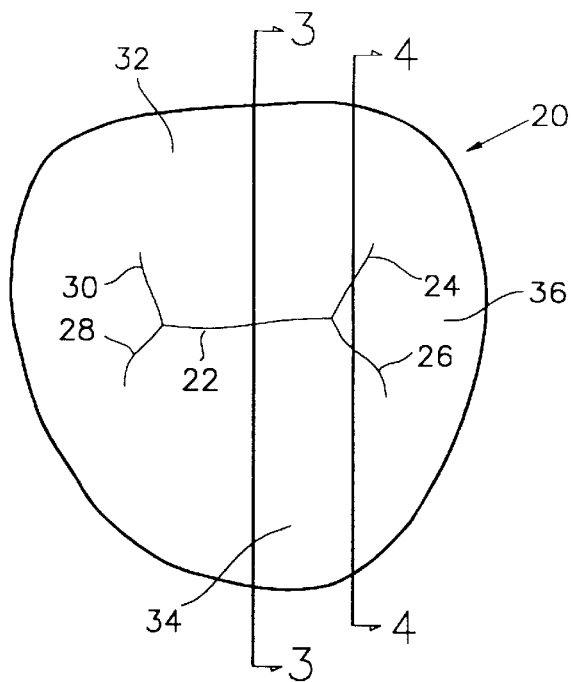
FIG. 2 is a plan view of an elastic lamina suited to application to the occlusal surface of the tooth shown in FIG. 1.
Figure 3:
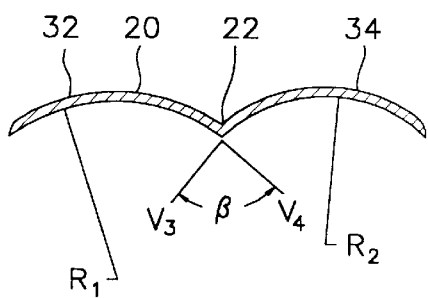
FIG. 3 is section of the elastic lamina of FIG. 2 along the lines 3—3.
Figure 4:
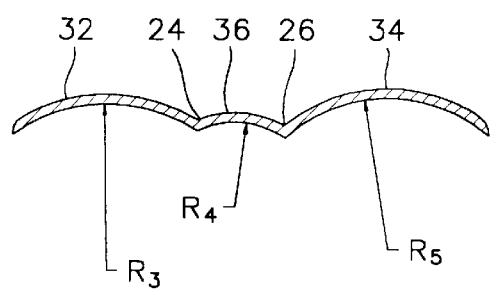
FIG. 4 is section of the elastic lamina of FIG. 2 along the lines 4—4.

Referring now to FIGS. 2, 3 and 4, the elastic lamina 20 has a central groove 22 corresponding to the central occlusal groove 10, a groove 24 corresponding to the mesiobuccal groove, a groove 26 corresponding to the mesiolingual groove, a groove 28 corresponding to the distolingual groove and a groove 30 corresponding to the distobuccal groove. On either side of the central groove 22 are concave wings 32 and 34 adapted to cover the buccal cusp 14 and lingual cusp 12 respectively. The word cusp or ridge is used here to refer to the material of the tooth between the perimeter of the occlusal surface and the groove. In addition, between the grooves 24 and 26, the material of the elastic lamina curves in a concave wing for use in covering the mesiomarginal ridge between the mesiobuccal groove and mesiolingual groove of the tooth. In addition, between the grooves 28 and 30, the material of the elastic lamina curves in a concave wing for use in covering the distomarginal ridge between the distobuccal groove and distolingual groove of the tooth.

The elastic lamina which forms the universal occlusal matrix for application to the occlusal surface OS of a tooth having a central groove forming a V-shape in cross-section such as is shown in FIG. 1, is transparent to ultraviolet rays and to rays of the visible spectrum to permit rapid hardening by polymerization of filling material used to fill a cavity in the tooth, and is made of a material which does not adhere to the filling material. Such material is well known in the art.

The central groove 22 forms a V-shape in cross-section as shown by the lines $V_3$ and $V_4$ in FIG. 2 with first and second curved concave wings 32 and 34 extending outward from the central groove. The angle of the V-shape defined by lines $V_3$ and $V_4$ is given by angle $\beta$. The areal extent of the elastic lamina 20 should be sufficient to just cover the entire occlusal surface of the teeth to which it may be applied. The areal extent may be greater, but any additional material beyond the occlusal surface is superfluous.

The angle $\beta$ of the V-shape of the groove of the lamina 20 is slightly greater than the angle $\alpha$ of the V-shape of the groove of the various teeth (But not so great as not to mimic the occlusal anatomy of teeth to which it may be applied. The same should also be true of the other grooves in the elastic lamina. That is, the angle of the V-shapes of the grooves of the elastic lamina should be greater than the angle of the corresponding grooves of the various teeth to which the lamina may be applied, but not so great as to not mimic the occlusal anatomy.

In addition, the wings 32, 34 and 36 should have radii of curvature $R_1$, $R_2$, $R_3$, $R_4$ and $R_5$ respectively less than the radius of curvature of the corresponding cusps or ridges of the various teeth to which it may be applied.

In this manner, the elastic lamina will not press down too head into a central occlusal groove during treatment, and will not force filling material out of a cavity in or near the central groove 10.

The teeth to which the elastic lamina may be applied are the maxillary left first premolar, the maxillary left second premolar, the mandibular left first premolar, the mandibular lost second premolar, the maxillary left first molar, the maxillary left second molar, the mandibular left first molar, the mandibular left second molar, and the corresponding right teeth. The occlusal surfaces of these teeth are described at pages 74–115 of "Dental Anatomy and Occlusion", Williams and Wilkins, Baltimore, 1969, the content of all of which is hereby incorporated herein by reference.

The elastic lamina of the invention has been described in relation to the maxillary second premolar but the same principles of construction apply to the other teeth mentioned here. For teeth with a large fossa, such as the mandibular first premolar, the fossa should be considered a groove, and the angle of the V-shaped portion of the elastic lamina extending into the fossa should be greater than the angle of the corresponding fossa.

The table following shows exemplary distances between elements of an elastic lamina suited to the corresponding features of the teeth mentioned in the table:

Table 1: Dimensions of Features of Elastic Lamina
Maxillary First Premolar
  Distance from mesial pit to buccal cusp tip: 2 mm
  Distance from mesial pit to lingual cusp tip: 1.5 mm
  Distance from distal pit to buccal cusp tip: 2 mm
  Distance from distal pit to lingual cusp tip: 1.5 mm
Maxillary Second Premolar
  Distance from mesial pit to buccal cusp tip: 2 mm
  Distance from mesial pit to lingual cusp tip: 1.5 mm
  Distance from distal pit to buccal cusp tip: 2 mm
  Distance from distal pit to lingual cusp tip: 1.5 mm
Mandibular First Premolar
  Distance from mesial groove to buccal cusp tip: 2 mm
  Distance from mesial groove to lingual cusp tip: 1.0 mm
  Distance from distal pit to buccal cusp tip: 2 mm
  Distance from distal pit to lingual cusp tip: 1.0 mm
Mandibular Second Premolar
  Distance from mesial pit to buccal cusp tip: 2 mm
  Distance from mesial pit to mesio-lingual cusp tip: 2 mm
  Distance from distal pit to buccal cusp tip: 2 mm
  Distance from distal pit to disto-lingual cusp tip: 1 mm
Maxillary First Molar
  Distance from central pit to mesio-lingual cusp tip: 3 mm
  Distance from central pit to mesiobuccal cusp tip: 2.5 mm
  Distance from central pit to distobuccal cusp tip 2.5 mm
  Distance from distal pit to disto-lingual cusp tip: 1.5 mm
  Distance from distal pit to distobuccal cusp tip: 2 mm
Maxillary Second Molar
  Distance from central pit to mesio-lingual cusp tip: 2.5 mm
  Distance from central pit to mesiobuccal cusp tip: 2.0 mm
  Distance from central pit to distal cusp tip: 2.0 mm
  Distance from distal pit to disto-lingual cusp tip: 1.0 mm
  Distance from distal pit to mesiobuccal cusp tip: 1.5 mm
Mandibular First Molar
  Distance from central pit to mesio-lingual cusp tip: 2.5 mm
  Distance from central pit to disto-lingual cusp tip: 2.0 mm
  Distance from central pit to mesiobuccal cusp tip: 2.5 mm
  Distance from central pit to distobuccal cusp tip: 2.5 mm
  Distance from central pit to distal cusp tip: 1.5 mm
  Distance from mesial pit to mesio-lingual cusp tip: 2.0 mm
  Distance from mesial pit to disto-lingual cusp tip: 1.5 mm
  Distance from mesial pit to mesiobuccal cusp tip: 2.0 mm
  Distance from mesial pit to distobuccal cusp tip: 2.0 mm
  Distance from distal pit to disto-lingual cusp tip: 1.5 mm
  Distance from distal pit to distobuccal cusp tip: 1.5 mm
  Distance from distal pit to distal cusp tip: 1.0 mm
Mandibular Second Molar
  Distance from central pit to mesio-lingual cusp tip: 2.0 mm
  Distance from central pit to disto-lingual cusp tip: 1.5 mm
  Distance from central pit to mesiobuccal cusp tip: 2.0 mm
  Distance from central pit to distobuccal cusp tip: 2.0 mm
  Distance from mesial pit to mesio-lingual cusp tip: 1.5 mm
  Distance from mesial pit to disto-lingual cusp tip: 1.0 mm
  Distance from mesial pit to mesiobuccal cusp tip: 1.5 mm
  Distance from mesial pit to distobuccal cusp tip: 1.5 mm
  Distance from distal pit to disto-lingual cusp tip: 1.0 mm
  Distance from distal pit to distobuccal cusp tip: 1.0 mm A person skilled in the art could make immaterial modifications to the invention described in this patent document without departing from the essence of the invention that is intended to be covered by the scope of the claims that follow.

The embodiments of the invention in which an exclusive property or privilege is claimed are defined as follows:

1. A universal occlusal matrix for application to the occlusal surface only of a tooth having a central groove forming a V-shape in cross section, the universal occlusal matrix consisting essentially of:

an elastic lamina made from a material that is transparent to ultraviolet rays and to rays of the visible spectrum to permit rapid hardening by polymerization of the filling material and which material does not adhere to that of the said filling;

the elastic lamina having a central groove forming a V-shape in cross-section with first and second curved concave wings extending outward from the central groove; and the elastic lamina extending away from the central groove sufficiently far to cover and mimic the occlusal surface only of a human tooth, wherein the human tooth is selected from the group consisting of the right and left maxillary first premolar, right and left maxillary second premolar, right and left mandibular first premolar, right and left mandibular second premolar, right and left maxillary first molar, right and left maxillary second molar, right and left mandibular first molar, and right and left mandibular second molar.

2. The universal occlusal matrix of claim 1 in which the elastic lamina mimics the occlusal surface only of one of the right and left maxillary first premolar.

3. The universal occlusal matrix of claim 1 in which the elastic lamina mimics the occlusal surface only of one of the right and left maxillary second premolar.

4. The universal occlusal matrix of claim 1 in which the elastic lamina mimics the occlusal surface only of one of the right and left mandibular first premolar.

5. The universal occlusal matrix of claim 1 in which the elastic lamina mimics the occlusal surface only of one of the right and left mandibular second premolar.

6. The universal occlusal matrix of claim 1 in which the elastic lamina mimics the occlusal surface only of one of the right and left maxillary first molar.

7. The universal occlusal matrix of claim 1 in which the elastic lamina mimics the occlusal surface only of one of the right and left maxillary second molar.

8. The universal occlusal matrix of claim 1 in which the elastic lamina mimics the occlusal surface only of one of the right and left mandibular first molar.

9. The universal occlusal matrix of claim 1 in which the elastic lamina mimics the occlusal surface only of one of the right and left mandibular second molar.

10. A set of universal occlusal matrices for application to the occlusal surface only of teeth having a central groove forming a V-shape in cross-section, the universal occlusal matrices each consisting essentially of:

an elastic lamina made from a material that is transparent to ultraviolet rays and to rays of the visible spectrum to permit rapid hardening by polymerization of the filling material and which material does not adhere to that of the said filling;

each elastic lamina having a central groove forming a V-shape in cross-section with first and second curved concave wings extending outward from the central groove; and each elastic lamina extending away from the central groove sufficiently far to cover and mimic the occlusal surface only of a different one of the human teeth selected from the group consisting of the right and left maxillary first premolar, right and left maxillary second premolar, right and left mandibular first premolar, right and left mandibular second premolar, right and left maxillary first molar, right and left maxillary second molar, right and left mandibular first molar, and right and left mandibular second molar.

11. A method of filling a tooth, wherein the tooth has an occlusal surface only having a central groove forming a V-shape in cross-section, the method consisting essentially of the steps of:

applying filling material to a cavity in the occlusal surface only of the tooth;

selecting an elastic lamina made from a material that is transparent to ultraviolet rays and to rays of the visible spectrum to permit rapid hardening by polymerization of the filling material and which material does not adhere to that of the said filling, the elastic lamina having a central groove forming a V shape in cross-section with first and second curved concave wings extending outward from the central groove, the elastic lamina extending away from the central groove sufficiently far to cover and mimic the occlusal surface only of the tooth;

applying the elastic lamina to the occlusal surface only of the tooth;

hardening the filling; and removing the elastic lamina from the tooth.

* * * * *